(12) United States Patent
Chiu et al.

(10) Patent No.: US 8,246,555 B2
(45) Date of Patent: Aug. 21, 2012

(54) METHOD AND SYSTEM FOR MONITORING SPORT RELATED FITNESS BY ESTIMATING MUSCLE POWER AND JOINT FORCE OF LIMBS

(75) Inventors: Yu-Hsien Chiu, Kaohsiung County (TW); Chi-Chun Hsia, Kaohsiung (TW); Pei-Jung Wang, Tainan (TW)

(73) Assignee: Industrial Technology Research Institute, Hsin-Chu (TW)

( * ) Notice: Subject to any disclaimer, the term of this patent is extended or adjusted under 35 U.S.C. 154(b) by 270 days.

(21) Appl. No.: 12/696,396

(22) Filed: Jan. 29, 2010

(65) Prior Publication Data
US 2011/0082394 A1  Apr. 7, 2011

(30) Foreign Application Priority Data
Oct. 7, 2009  (TW) ................................ 98133931 A (51) Int. Cl.
*A61B 5/103* (2006.01)
(52) U.S. Cl. ................. 600/595; 482/1; 482/8; 482/901
(58) Field of Classification Search .................. 482/1–9, 482/900–902; 600/595; 434/247; 702/41
See application file for complete search history.

(56) References Cited

U.S. PATENT DOCUMENTS

| | | | |
|---|---|---|---|
| 6,331,893 B1 | 12/2001 | Brown et al. | |
| 6,846,270 B1 * | 1/2005 | Etnyre | 482/6 |
| 7,927,253 B2 * | 4/2011 | Vincent et al. | 482/9 |
| 2009/0076419 A1 | 3/2009 | Namineni et al. | |
| 2011/0208444 A1 * | 8/2011 | Solinsky | 702/41 |

FOREIGN PATENT DOCUMENTS

| | | |
|---|---|---|
| JP | 2001061817 A | 3/2001 |
| JP | 2008104667 A | 5/2008 |
| JP | 2009082428 A | 4/2009 |
| TW | I275045 B | 3/2007 |
| TW | M319674 U | 10/2007 |
| TW | M342870 U | 10/2008 |
| TW | I307635 B | 3/2009 |

OTHER PUBLICATIONS

Japan Patent Office, "Office Action", Jan. 24, 2012, Japan.
Japan Patent Office, "Allowance", May 15, 2012.

\* cited by examiner

*Primary Examiner* — Glenn Richman
(74) *Attorney, Agent, or Firm* — Morris, Manning & Martin, LLP; Tim Tingkang Xia, Esq.

(57) ABSTRACT

The present invention relates to a method and system for monitoring sport related fitness by estimating muscle power and joint force of limbs, in which the system comprises a sensing module and a force/track detection module, wherein sensor values from the sensing module are fed to the force/track detection module to be used as base for estimating feature parameters and classifying a motion series relating to muscle power and joint force of limbs so as to obtain skill-related fitness parameters corresponding to the sensing of the sensor module.

24 Claims, 5 Drawing Sheets

METHOD AND SYSTEM FOR MONITORING SPORT RELATED FITNESS BY ESTIMATING MUSCLE POWER AND JOINT FORCE OF LIMBS

TECHNICAL FIELD

The present disclosure relates to a method and system for monitoring sport related fitness, and more particularly, to a fitness monitoring method and system capable of performing a fitness evaluation at any time and place since it is not only configured with a monitor platform adapted to be arranged in any common household living space, but also with a portable fitness detection module.

TECHNICAL BACKGROUND

Research has shown that a large number of the health problems in society are either caused in whole or in part by an unhealthy lifestyle that often result in poor eating habits, high stress levels, lack of exercise, poor sleep habits, and so on. Recognizing this fact, the field of physical fitness assessment and testing has seen an increasing demand with rising public interest in physical fitness and the relevance of performance to soldiers, firefighters, athletes, and the like. Moreover, it is used in the field of patient rehabilitation. These days, physical fitness is considered a measure of the body's ability to function efficiently and effectively in work and leisure activities, to be healthy, to resist hypokinetic diseases, and to meet emergency situations. Accordingly, a general-purpose physical fitness program must address the following essentials: cardio-respiratory endurance, muscular strength and muscular endurance, joint flexibility, and body composition, which are health related issues, However, the sport-related issues are also included, which are muscular power, agility, speed and coordination, etc. Scoring high on those physical fitness assessments usually indicates better heath and better exercise performance. However, good physical fitness is not easy to obtain and certainly can not be achieved overnight. It requires a person to maintain a healthy lifestyle while exercise in a regular basis. Nevertheless, for motivating a person to live a healthier life and exercise regularly, it would be a great help if data of detailed physical fitness can be provided to that person in a daily basis to be used as a guide for achieving a healthier lifestyle, for monitoring progress, and for brainstorming solutions when problems arise.

Conventionally, a fitness assessment is a series of measurements that help determine physical fitness. The basic formula of any conventional fitness assessment is to evaluate body mass index (BMI), resting heart rate and blood pressure, and aerobic fitness before, during or after a moderate workout that may last a specific period of time. There are many fitness assessment products available on the market, including weight scales with BMI monitoring ability and tread mills with heart rate/respiratory monitoring ability, and so on. However, all those fitness assessment products have the following shortcomings:

(1) The fitness assessment can only be conducted on the specific exercise platform;

(2) The result of the fitness assessment can be very subjective since it is provided from assessors sometimes only basing on the readings from those fitness assessment products while those assessors might not be particularly well trained;

(3) Those products with balance evaluation system are imported that are bulky and expensive;

(4) It is required for the user to be applied by at least a set of electrodes for enabling a wireless or wired EMG test to be perform;

(5) In those conventional fitness assessment products, it is common to use a game console, such as Wii fit, for motivating its users to perform the designated exercises. However, such game console neither is not appropriate for elders, nor is not therapeutic effective in clinical practice;

(6) There is no dynamic balance monitoring for the control of the nervous, muscular and skeletal systems relating to the motions of upper and lower limbs that is available in conventional fitness assessment products with game console; and (7) The conventional fitness assessment products with game console are not designed with the ability relating to the recognizing of motion accuracy and coordination.

TECHNICAL SUMMARY

The present disclosure relates to a fitness monitoring method and system capable of performing a fitness evaluation at any time and place since it is not only configured with a monitor platform adapted to be arranged in any common household living space, but also with a portable fitness detection module.

In an exemplary embodiment, the present disclosure provides a method and system for monitoring sport related fitness, in which the system comprises: a sensing module and a force/track detection module, wherein sensor values from the sensing module are fed to the force/track detection module to be used as base for estimating feature parameters and classifying a motion series relating to muscle power and joint force of limbs so as to obtain skill-related fitness parameters corresponding to the sensing of the sensor module.

Further scope of applicability of the present application will become more apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given herein below and the accompanying drawings which are given by way of illustration only, and thus are not limitative of the present disclosure and wherein.

DESCRIPTION OF THE EXEMPLARY EMBODIMENTS

For your esteemed members of reviewing committee to further understand and recognize the fulfilled functions and structural characteristics of the disclosure, several exemplary embodiments cooperating with detailed description are presented as the follows.

Figure 1:
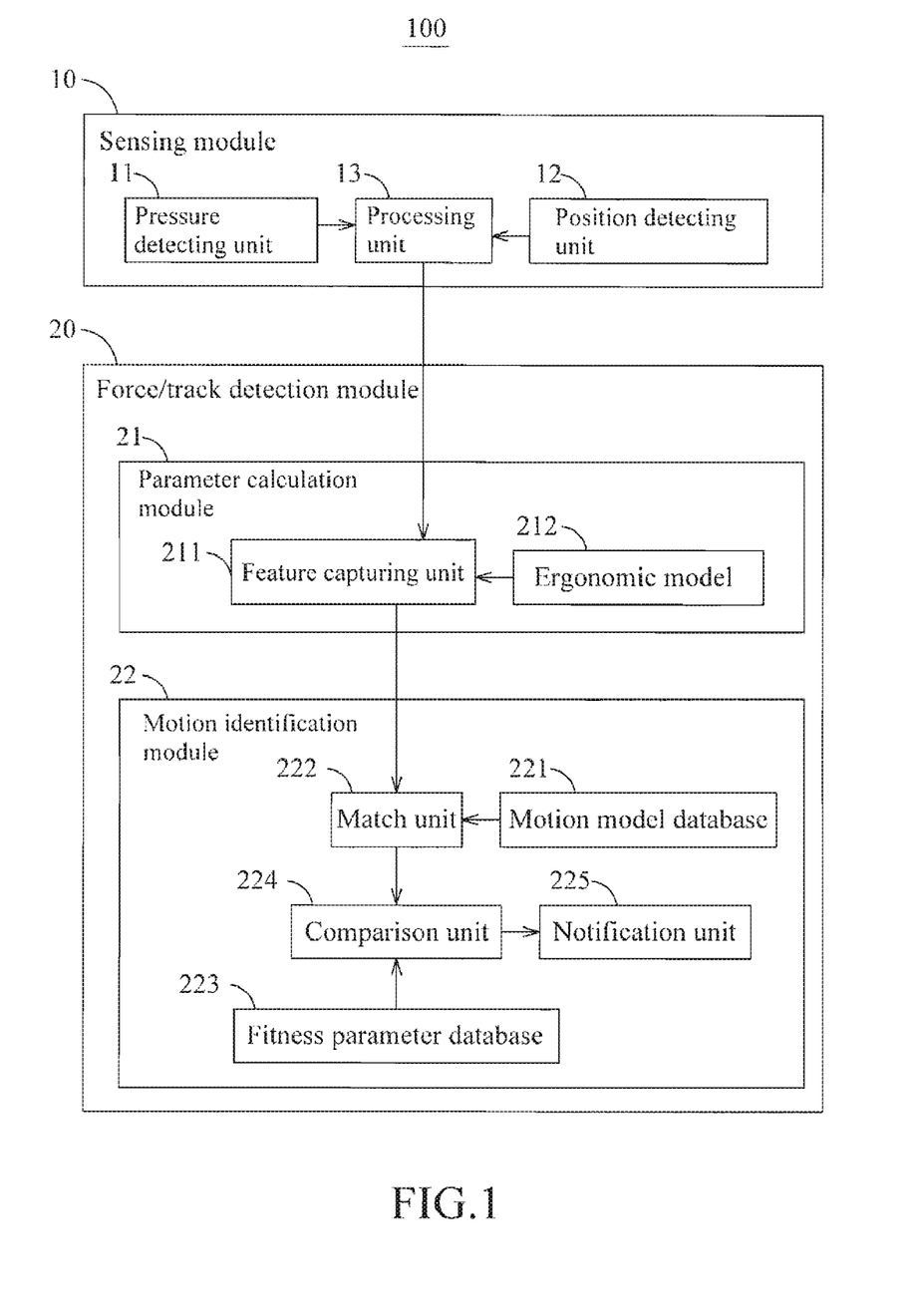
FIG. 1 is a block diagram of a system for monitoring sport related fitness according to an exemplary embodiment of the present disclosure.

Please refer to FIG. 1, which is a block diagram of a system for monitoring sport related fitness according to an exemplary embodiment of the present disclosure. IN FIG. 1, the system for monitoring sport related fitness is primarily composed of: a sensing module 10 and force/track detection module 20.

The sensing module 10 is configured with a pressure detecting unit 11, a position detecting unit 12 and a processing unit 13, in which the pressure detecting unit 11, being used for sensing a value relating to pressure, can be a device selected from the group consisting of: a pressure mat, a foot pad, and a force plate, that is provided for a user to step thereon so as to generate a pressure value accordingly; the position detecting unit 12, being used for sensing a value relating to motion track, can be a device including at least one device selected from the group consisting of: accelerometers and gyroscopes that can be adapted to be arranged at an arm, an elbow, waist, or a knee of a user; and the processing unit 13 is used for fetching and synchronizing the sensor values, such as the aforesaid pressure values from the pressure detecting unit 11 and the motion track values from the position detecting unit 12.

It is noted that by arranging the pressure detecting unit 11 and the position detecting unit 12 at different positions of a user, the limb motions of the user capable of being detected thereby can be different. For any human body, the force/track detection module 10 is enabled to tracking an exercise performed by the limbs of the user, which includes upper limbs such as arms and lower limbs such as legs, while the detected track is resulting from at least one exercise selecting from the group consisting of: the stretching exercise of the upper limbs and the stretching exercise of the lower limbs. Moreover, the stretching exercise of the upper limbs includes at least one movement selected from the group consisting of: lifting a heavy object, pushing/pulling, punching, racket swinging, and pitching; and the stretching exercise of the lower limbs includes at least one movement selected from the group consisting of: one foot lifting, one leg squatting, one leg standing, two legs standing. By attaching the position detecting unit 12 to one upper limb or lower limb of the user, the motion track of such upper limb or lower limb can be sensed thereby. In the present disclosure, the user is allowed to have one of his/her upper limb, one of his/her lower limb, both of his/her upper limb, both of his/her lower limb, or even one selected upper limb and one selected lower limb, to be mounted by the position detecting unit 12 at will. In addition, when the user, having the position detecting unit 12 attached therein, is stepped on the pressure detecting unit 11 while performing an exercise, the force variation relating to the exercise of the user can be detected thereby as simultaneously the motion track relating to the exercise is detected by the position detecting unit 12.

The force/track detection module 20 is provided for receive the sensor values from the sensing module 10 to be used as base for estimating feature parameters and classifying a motion series relating to muscle power and joint force of the limbs so as to obtain fitness parameters corresponding to the sensing of the sensor module. Moreover, the force/track detection module 20 includes a parameter calculation module 21 and a motion identification module 22.

The parameter calculation module 21 is primarily composed of a feature capturing unit 211 and an ergonomic model database 212. The feature capturing unit 211 is used for fetching the sensor values from the sensing module to be used in an estimation for obtaining the feature parameters relating to muscle power and joint force of the limbs, in which each feature parameter is related to at least one value selected from the group consisting of: gravity center of human body, biped center of mass, displacement of the center of gravity, direction, speed, distance traveled, relative position, coefficient of rigidity, joint angle, variation of joint angle, muscle power. The ergonomic model database 212 is used for storing data relating to ergonomic models to be used as basis for estimating the feature parameters.

The motion identification module 22 is composed of a motion model database 221, a match unit 222, a fitness parameter database 223, a comparison unit 224 and a notification unit 225. The motion model database 221 has the at least one motion track model stored therein, whereas each motion track model is at least one model selected from the group consisting of: a motion track templet, a motion track statistic model, a motion track probabilistic model. The match unit 222 is used for performing the matching calculation, such as a distance calculation or a similarity calculation, upon the feature parameter resulting from the estimation of the parameter calculation module 21 and the at least one motion track models form the motion model database 221 so as to obtain an optimal motion track corresponding to the feature parameters to be classified into the motion series that is used for estimating the fitness parameters. Moreover, the fitness parameter is related to at least one value selected from the group consisting of: muscular strength, muscular endurance, agility, flexibility, muscle power, speed, and balance.

The fitness parameter database 223 is provided for storing skill-related fitness parameters while providing the stored skill-related fitness parameters to be compared with the fitness parameters obtained from the estimation of the motion identification module 22. The comparison unit 224 is used for comparing the fitness parameters obtained from match unit 222 with the skill-related fitness parameters stored in the fitness parameter database 223 so as to output a comparison result accordingly. Moreover, the notification unit 225 is used for displaying the comparison result as it is electrically connected to the comparison unit 224, and thus the notification unit 225 can be a device selected from the group consisting of: cellular phones, personal digital assistants (PDAs), computers, speakers, alarms, indication lamps, and other audio/video devices, that is capable of connecting to the comparison unit 224 in a wired or wireless manner, i.e. by cable or through a network system for instance.

Figure 2:
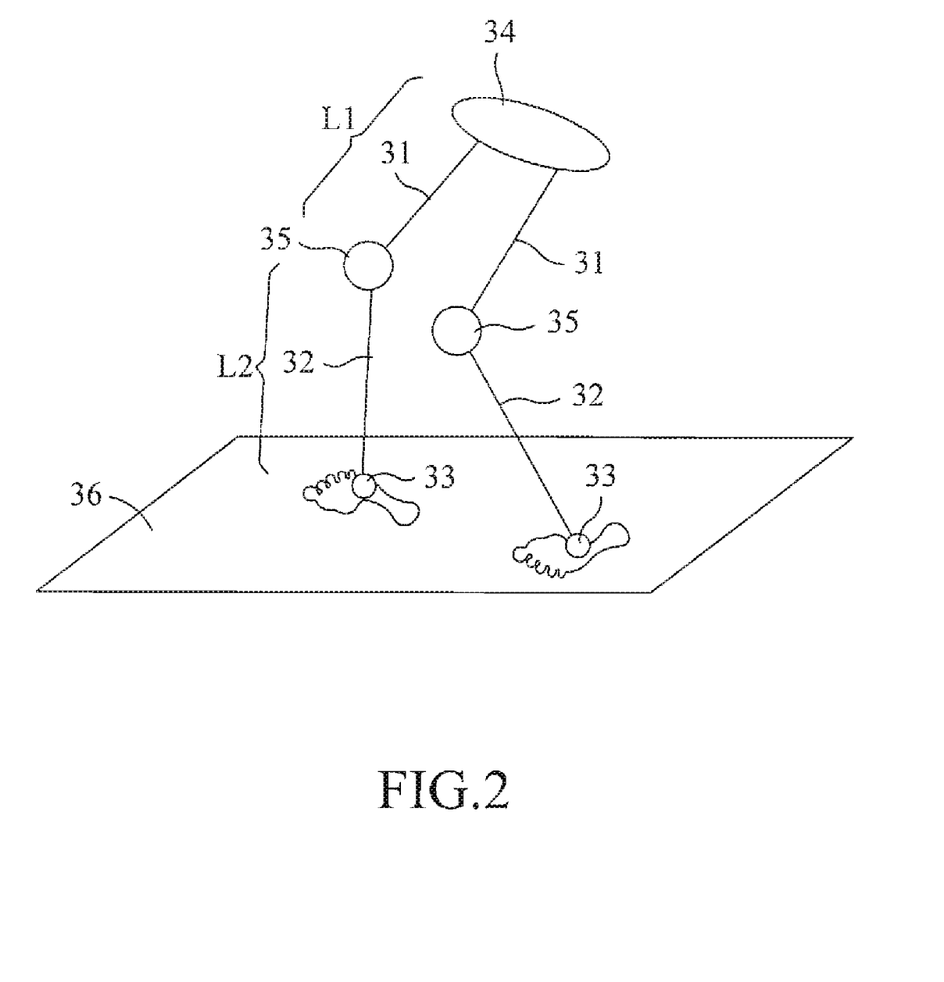
FIG. 2 is a schematic diagram showing the coordination of shanks and thighs of lower limbs in an ergonomic model used in the present disclosure.

Please refer to FIG. 2, which is a schematic diagram showing the coordination of shanks and thighs of lower limbs in an ergonomic model used in the present disclosure. In FIG. 2, each thigh 31 is referred as a first limb L1 while the corresponding shank 32 along with the foot 33 are referred as a second limb L2, in which the upper end of the first limb L1 is connected to a widesence stationary end 34 whereas the widesence stationary end 34 includes the hip joint, the pelvic cavity and the lumbar vertebra; and the lower end of the first limb L1 is connected to the knee joint 35. Moreover, the upper end of the second limb L2 is connected to the knee joint 35 while the lower end thereof is connected to the foot 33 as the foot 33 is stepping on a planar surface 36. When the foot 35 is subjected to a force of any direction, there will be a reacting force acting on the knee joint 35 according to the Newton's third laws of motion, and thus, in order to keep balance, it s required for the knee joint 35 to generate a force for counterbalancing the reacting force. At this moment, since the station end 34 is in the status of widesence stationary, only the knee joint 35 will be caused to rotate by the torque resulting from the force of counterbalancing that the addition of the displacement vectors relating to the knee joint 35 and the foot 33 will construct a nonlinear relationship. Therefore, with respect to the rigidity of the foot 33, the relationship between the displacements and forces working on the foot 33 and the knee joint 35 can be defined and described by a matrix.

As shown in FIG. 1 and FIG. 2, assuming the foot 33 on the planar surface 36 is subjected to a force representing as $[F_X, F_Y]$, such force $[F_X, F_Y]$ is detected by the sensing module 10 so as to be fed into the parameter calculation module 21 of the force/track detection module 20. Moreover, the stiffness of the foot 33 is an 2×2 endpoint stiffness matrix obtained by performing a partial differential calculation upon the known restoring forces and displacements in the x-axis and y-axis directions. It is noted that the aforesaid stiffness matrix can not be a diagonal matrix or a determinat matrix that is a zero matrix. For keeping the entire lower limbs shown in FIG. 2 to move without tipping off and the whole chain of motions in the lower limbs in a stable balance state, the aforesaid stiffness matrix must be a symmetric matrix, i.e. $S_{xy}=S_{yx}$, that is defined in the following equations:

$$dF_X = -\left(\frac{\partial F_X}{\partial X}dX + \frac{\partial F_X}{\partial Y}dY\right) = -(S_{XX}dX + S_{XY}dY)$$

$$dF_Y = -\left(\frac{\partial F_Y}{\partial X}dX + \frac{\partial F_Y}{\partial Y}dY\right) = -(S_{XY}dX + S_{YY}dY)$$

$$\begin{bmatrix} dF_X \\ dF_Y \end{bmatrix} = -\begin{bmatrix} \frac{\partial F_X}{\partial X} & \frac{\partial F_X}{\partial Y} \\ \frac{\partial F_Y}{\partial X} & \frac{\partial F_Y}{\partial Y} \end{bmatrix} \begin{bmatrix} dX \\ dY \end{bmatrix} = -[S]\begin{bmatrix} dX \\ dY \end{bmatrix}$$

$$[S] = \begin{bmatrix} \frac{\partial F_X}{\partial X} & \frac{\partial F_X}{\partial Y} \\ \frac{\partial F_Y}{\partial X} & \frac{\partial F_Y}{\partial Y} \end{bmatrix}$$

where, $dF_X$ is the differentiation of $F_X$ with respect to displacement;
$dF_Y$ is the differentiation of with respect to displacement;
$S_{XY}=\partial F_X/\partial Y$, is the partial differentiation of $F_X$ with respect to displacement in Y-axis direction;
$S_{YX}=\partial F_Y/\partial X$, is the partial differentiation of $F_Y$ with respect to displacement in X-axis direction;
$S_{XX}=\partial F_X/\partial X$, is the partial differentiation of $F_X$ with respect to displacement in X-axis direction;
$S_{YY}=\partial F_Y/\partial Y$, is the partial differentiation of $F_Y$ with respect to displacement in Y-axis direction; and
[S] is a stiffness matrix representing the stiffness of the foot 33.

Assuming the biped system shown in FIG. 2 is under a certain balance control ($0<\phi<2\pi$) whereas the foot on the planar surface 36 is affected to moved in multiple directions with a minimum displacement, the displacement of the foot 33 can be represented as $[dX,dY]=[\cos\phi,\sin\phi]$, and the restoring force in x-axis direction and y-axis direction can be defined as following:

$$F_X=-(S_{XX}\cos\phi+S_{XY}\sin\phi)$$

$$F_Y=-(S_{YX}\cos\phi+S_{YY}\sin\phi)$$

Figure 3:
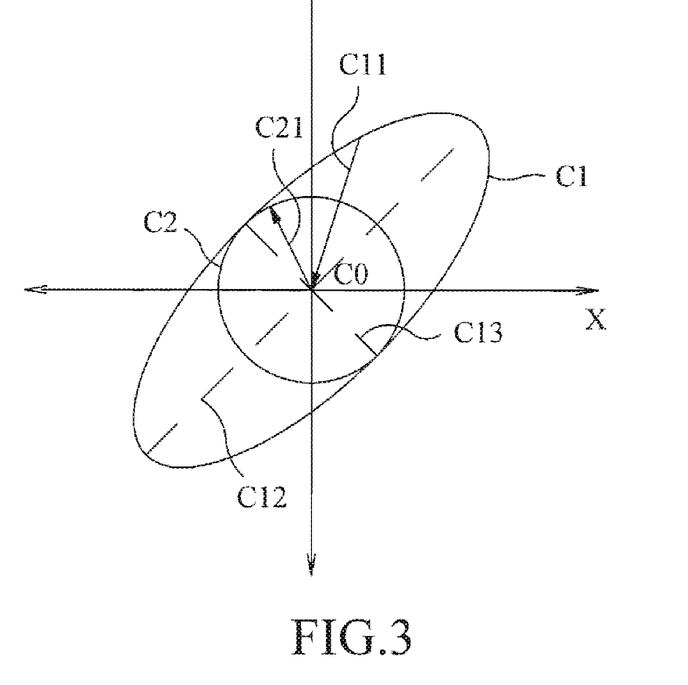
FIG. 3 is a schematic diagram showing the relationship between sport-related fitness and a stiffness elliptic inclusion according to the present disclosure.

When the direction of the displacement is varied from 0 degree to 360 degrees, a stiffness ellipse can be obtained, as the one shown in FIG. 3. In FIG. 3, the line C11 connecting a random point on the stiffness ellipse C1 and the center thereof indicates the magnitude of the restoring force required when the selected random point is shifted from its current stable balance state by a unit displacement C21. The stiffness ellipse C1 is defined by the following equation:

$$\frac{F_X^2}{\left(\sqrt{2}\,(S_{XX}\cos\varphi + S_{XY}\sin\varphi)\right)^2} + \frac{F_Y^2}{\left(\sqrt{2}\,(S_{YX}\cos\varphi + S_{XY}\sin\varphi)\right)^2} = 1$$

In the stiffness ellipse C1, the long axis indicates the direction of maximum restoring force, so that it is referred as the maximal stiffness axis; and on the other hand, the short axis thereof is referred as the minimal stiffness axis. Let the length of the long axis C12 to be 2a and that of the short axis C13 to be 2b, the following equation can be obtained:

$$2a=2\sqrt{2}(S_{XX}\cos\phi+S_{XY}\sin\phi)$$

$$2b=2\sqrt{2}(S_{YX}\cos\phi+S_{YY}\sin\phi)$$

Accordingly, under balance control, the length of the long axis C12 should equal to that of the short axis C13, so that the stiffness ellipse C1 is substantially conformed to the circle C2.

The operation principle of motion track identification performed by the motion identification module 22 is described in the following with reference to FIG. 1. In a motion identification operation, when an stretching exercise is performed and detected by the sensing module 10, the sensor values corresponding to the stretching exercise will be issued by the sensing module 10 that are received by the parameter calculation module 21 to be used in a calculation for obtaining feature parameters relating to muscle power and joint force of the limbs. Then, the obtained feature parameters are fed to the motion identification module 22, in which the match unit 22 is enabled to perform a matching calculation upon the feature parameters and the motion track models so as to obtain an optimal motion track corresponding to the feature parameters according to the similarity between the vector of the feature parameters and the compared motion track model, which can be represented by a probability $P(X|C_k)$ in the present embodiment, and simultaneously, a GMM (Gaussian Mixture Model) is used as the motion track model, which are defined by the following equation:

$$P(X\mid C_k) = \prod_{t=1}^{T} P(x_t\mid \Lambda_k) = \sum_{t=1}^{T} \log P(x_t\mid \Lambda_k)$$

$$= \sum_{t=1}^{T} \log\left(\sum_{m=1}^{M_k} w_{k,m} N\!\left(x_t;\mu_{k,m},\sum_{k,m}\right)\right)$$

-continued $$= \sum_{t=1}^{T} \log \left( \sum_{m=1}^{M_k} w_{k,m} \frac{|\Sigma_{k,m}|^{1/2}}{(2\pi)^d} \exp\left(-\frac{1}{2}(x_t - \mu_{k,m})^T \sum_{k,m}^{-1}(x_t - \mu_{k,m})\right) \right)$$

wherein, $X = \{x_1, x_2, \ldots, x_t, \ldots x_T\}$ represents the vector of feature parameters obtained from the calculation of the parameter calculation module that is fed into the motion identification module, and $x_t \in R^d$;

$C_k$ represents the $k^{th}$ type movement in a motion track;

$\Lambda_k$, represents the model parameters of the $k^{th}$ type of movement;

$P(x_t|\Lambda_k)$ is the probability model for each type of movement, being a GMM (Gausian Mixture model) that it is composed of: weights $w_{k,m}$ for each mixture, expected value vectors $\mu_{k,m}$ of each Gaussian distribution, and covariance matrixes $\Sigma_{k,m}$, whereas those parameters and weights are obtained using an Expectation-Maximaization (EM) algorithm.

Figure 4:
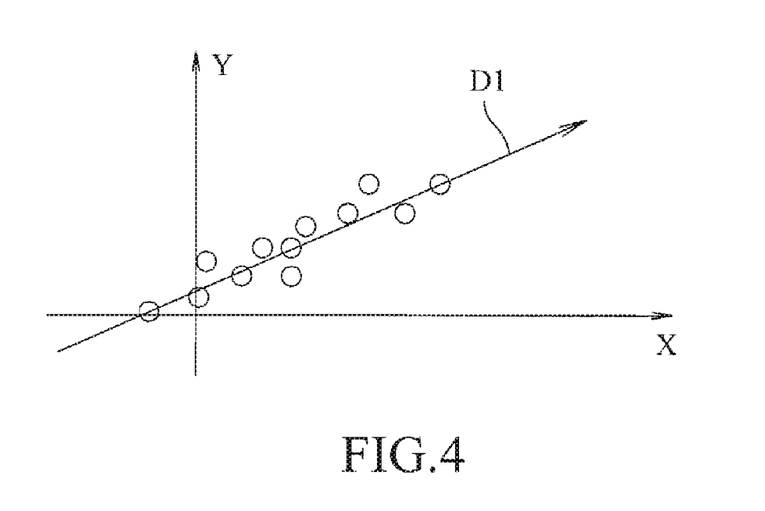
FIG. 4 is a schematic diagram showing an identification projection of the present disclosure.

For further modeling a motion for identification, a Latent Semantic Analysis (LSA) is introduced for converting those feature parameters to an identification space where they can be trained to be used in a later classification process, as that shown in FIG. 4, by that the projection direction D1 of maximal identification effectiveness is found.

In the present embodiment, a method of singular value decomposition (SVD) is used for locating the optimal discriminative matrix $T^T$ to be used for converting those feature parameters to the identification space, and then training the model parameters $\Lambda_k$ of each $C_k$ for fitting the result with a Gaussian Mixture Model so as to achieve the aforesaid modeling.

The aforesaid algorithm is defined by the following equation:

$$P(X | C_k) \approx P(T^T X | C_k)$$

$$= \prod_{t=1}^{T} P(\hat{x}_t | \hat{\Lambda}_k)$$

$$= \sum_{t=1}^{T} \log P(\hat{x}_t | \hat{\Lambda}_k)$$

$$= \sum_{t=1}^{T} \log \left( \sum_{m=1}^{M_k} \hat{w}_{k,m} N\left(\hat{x}_t; \hat{\mu}_{k,m}, \hat{\Sigma}_{k,m}\right) \right)$$

$$= \sum_{t=1}^{T} \log \left( \sum_{m=1}^{M_k} \hat{w}_{k,m} \frac{|\hat{\Sigma}_{k,m}|^{1/2}}{(2\pi)^d} \exp\left(-\frac{1}{2}(\hat{x}_t - \hat{\mu}_{k,m})^T \hat{\Sigma}_{k,m}^{-1}(\hat{x}_t - \hat{\mu}_{k,m})\right) \right)$$

wherein $\hat{x}_t$ and $\hat{\Lambda}_k = \{\hat{w}_{k,m}, \hat{\mu}_{k,m}, \hat{\Sigma}_{k,m}; 1 \leq m \leq M_k\}$ represent the feature parameters and the model parameters in the identification space, by that, during the classification, the model similarity calculation is performed using the probability model $P(X|C_k) \approx P(T^T X|C_k)$ that is projected in the identification space.

Figure 5:
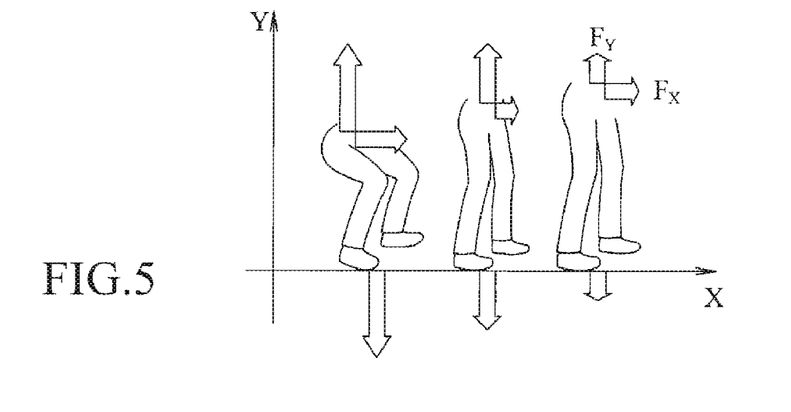
FIG. 5 shows a motion of a lower limb with respect to the variation of force direction during the motion according to the present disclosure.
Figure 6:
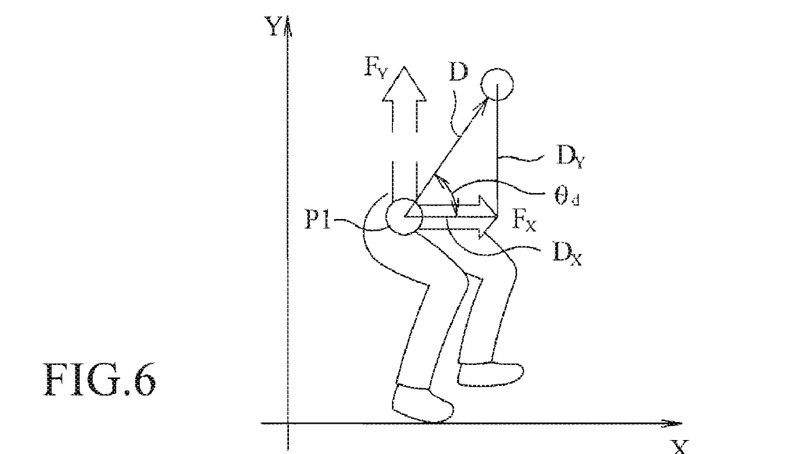
FIG. 6 is a schematic diagram showing the detection of a lower limb motion according to an embodiment of the present disclosure.
Figure 7:
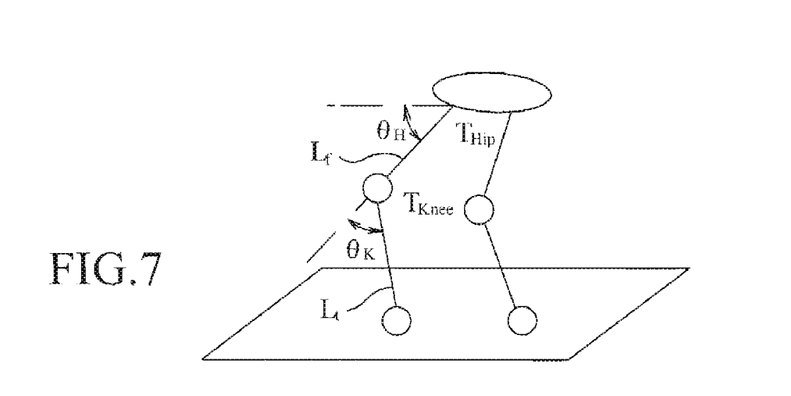
FIG. 7 is a schematic diagram showing how the joint angles in lower limb are related to each other.

Please refer to FIG. 5 to FIG. 7, which show a motion of a lower limb with respect to the variation of force direction during the motion according to the present disclosure. According to the monitoring system shown in FIG. 1 when it is used for detecting the motion of lower limbs, it can use a pressure mat as its pressure detecting unit 11 while attaching an accelerometer or gyroscope to be used as the position detecting unit 12.

In FIG. 5, the body mass center, i.e. the waist, is defined to be the end point of an lower-limb model, in which:

$F_X$: basing on $F=ma$, it is the product of body mass with the second order time differentiation of body gravity center movement;

$F_Y$: basing on the Newton's third laws of motion, it is the product of the sensing area with the total instant pressure detected by the pressure mat.

Please refer to FIG. 6, which is a schematic diagram showing the detection of a lower limb motion according to an embodiment of the present disclosure. In FIG. 6, P1 is the mass center of the body; D is the total displacement length of the body mass center P1 during the standing-up movement in centimeter (cm); $D_x$ is the length of displacement in X-axis direction in centimeter (cm); $D_y$ is the length of displacement in Y-axis direction in centimeter (cm); and $\theta_d$ is the included angle between D and $D_x$.

Please refer to FIG. 7, which is a schematic diagram showing how the joint angles in lower limb are related to each other. In FIG. 7, $L_f$ is the length of the thigh; $L_t$ is the length of the shank; $\theta_H$ is the stretching angle of the hip joint; $\theta_K$ is the stretching angle of the knee joint; $T_{Hip}$ is the torque exerting on the hip joint; and $T_{knee}$ is the torque exerting on the knee joint. Thereby, the relationship of angle variation with respect to the forces and torques exerting on the joints is defined as following:

$$\begin{bmatrix} T_{Hip} \\ T_{Knee} \end{bmatrix} = \begin{bmatrix} F_X \\ F_Y \end{bmatrix} \cdot J^T = [S] \begin{bmatrix} dX \\ dY \end{bmatrix}$$

$$J = \begin{bmatrix} -L_f \sin(\theta_H) - L_t \sin(\theta_H + \theta_K) & -L_t \sin(\theta_H + \theta_K) \\ L_f \cos(\theta_H) + L_t \cos(\theta_H + \theta_K) & L_t \cos(\theta_H + \theta_K) \end{bmatrix}$$

Figure 8:
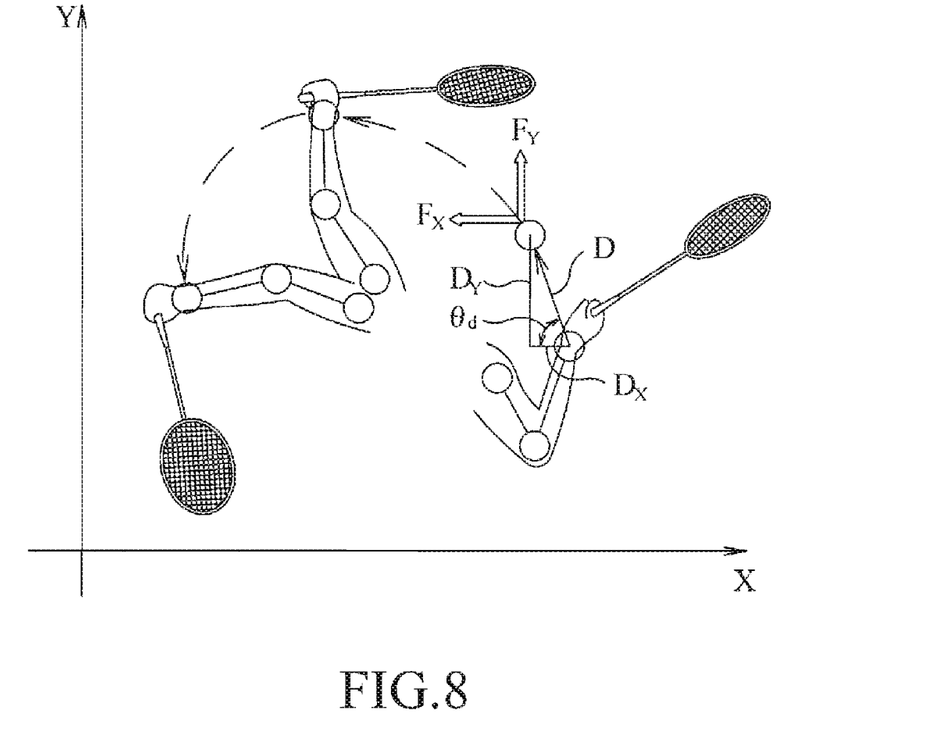
FIG. 8 is a schematic diagram showing the detection of an upper limb motion according to an embodiment of the present disclosure.
Figure 9:
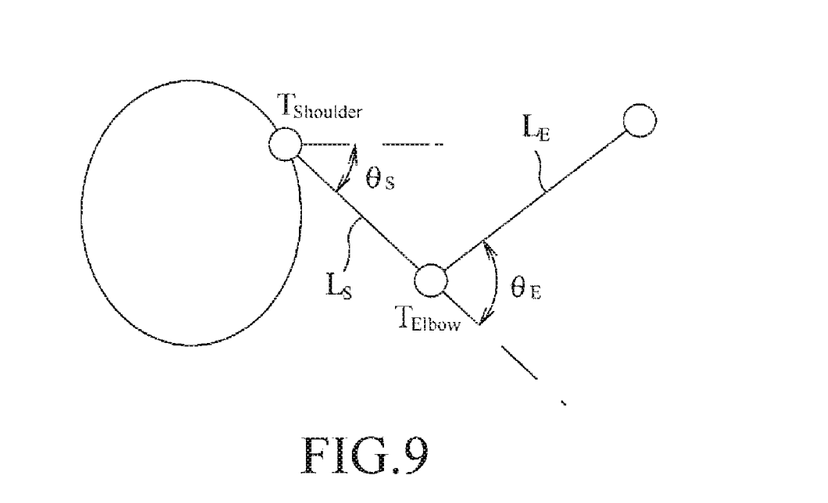
FIG. 9 is a schematic diagram showing how the joint angles in upper limb are related to each other.

Please refer to FIG. 8 and FIG. 9, which show a motion of an upper limb with respect to the variation of force direction during the motion according to the present disclosure. In FIG. 8, the motion performed by the upper limb is a racket swinging movement. According to the monitoring system shown in FIG. 1 when it is used for detecting the motion of upper limb, it can attach accelerometers at the user's shoulder joint, elbow joint, and wrist joint to be used as the position detecting units 12, that are able to detect the smoothness of the racket swinging movement in a continuous manner.

In FIG. 8, D is the average wrist displacement length during the racket swinging movement in centimeter (cm); $D_x$ is the length of displacement in X-axis direction in centimeter (cm); $D_y$ is the length of displacement in Y-axis direction in centimeter (cm); and $\theta_d$ is the included angle between D and $D_x$.

In FIG. 9, Ls is the length of the upper arm; Lt is the length of the lower arm; $\theta_S$ is the included angle between the shoulder joint and the elbow joint; $\theta_E$ is the included angle between the upper arm and the lower arm; $T_{shoulder}$ is the torque exerting on the shoulder joint; and $T_{elbow}$ is the torque exerting on the elbow joint. Thereby, the relationship of angle variation with respect to the forces and torques exerting on the joints is defined as following:

$$\begin{bmatrix} T_{shoulder} \\ T_{elbow} \end{bmatrix} = \begin{bmatrix} F_X \\ F_Y \end{bmatrix} \cdot J^T = [S]\begin{bmatrix} dX \\ dY \end{bmatrix}$$

$$J = \begin{bmatrix} -L_S \sin(\theta_S) - L_E \sin(\theta_S + \theta_E) & -L_E \sin(\theta_S + \theta_E) \\ L_S \cos(\theta_S) + L_E \cos(\theta_S + \theta_E) & L_E \cos(\theta_S + \theta_E) \end{bmatrix}$$

The system and method disclosed in the present disclosure not only can be applied in the field of exercise, but also can be applied in medical applications, such as the risk quantification and comparison for the elders or the mobility disabled.

By using the monitoring system shown in FIG. 1 in a manner that: there are pressure mats being used as the pressure detecting unit 11 and disposed at locations of highest risk of falling down, such as areas near the gateway of a stair, bed sides, areas in front of a stool, and there are accelerometers or gyroscopes being used as the position detecting units and attached to the belt of the user for detecting information relating to the user's movement. Thereby, sport-related fitness parameters can be estimated and calculated by the parameter calculation module 21 and the motion identification module 22 to be used in a risk assessment for quantifying the risk of falling down in a stepwise manner, i.e. high risk, middle risk and low risk, so that as soon as an assessment indicating high risk, the system will be enabled to issue a warning signal in a wired or wireless manner.

Regarding to the risk quantification and comparison and assuming there are q risk assessment indexes of falling representing as $y=\lfloor y_1, \ldots, y_q \rfloor$, and there are p parameters in the sport-related fitness parameters representing as $x=\lfloor x_1, \ldots, x_p \rfloor$, the method for risk quantification and comparison is designed to find the parameters in the p sport-related fitness parameters that are most correlated with the risk assessment indexes. According to the monitoring system shown in FIG. 1, after receiving the fitness parameters estimated and obtained from the match unit 222, the comparison unit 224 is enabled to compare the estimated fitness parameters with the skill-related fitness parameters stored in the fitness parameter database 223 so as to output a comparison result accordingly; and if the comparison result is in the neighborhood of a high risk value of falling down, the notification unit 225 is enabled to issue a warning signal.

The canonical correlation analysis is used for finding the fitness parameters that are most correlated with the risk assessment indexes. That is, in statistics, canonical correlation analysis is a way of making sense of cross-covariance matrices. If we have two sets of variables, $\tilde{x}=a'_1 x$, $a_1 = \lfloor a_{1,1}, \ldots, a_{1,p} \rfloor$, $\tilde{y}=b'_1 y$, $b_1 = \lfloor b_{1,1}, \ldots, b_{1,q} \rfloor$ and there are correlations among the variables, then canonical correlation analysis will enable us to find linear combinations of the $\tilde{x}$ and the $\tilde{y}$ which have maximum correlation with each other. That is, one seeks vectors maximizing the equation of $$a'_1 \sum_{xy} b_1$$

subject to the constraint that:
$a'_1 \Sigma_{xx} a_1 = 1$ and $b'_1 \Sigma_{yy} b_1 = 1$. Mathematically, the feature vector that is corresponded to the largest eigenvalue $$\lambda_1 \text{ of } \sum_{xx}^{-1} \sum_{xy} \sum_{yy}^{-1} \sum_{yx} \text{ is}$$

is $a_1$ whereas the eigenvalue $\lambda_1$ is able the largest eigenvalue $$\sum_{yy}^{-1} \sum_{yx} \sum_{xx}^{-1} \sum_{xy}$$

of whose corresponding feature vector will be $b_1$.

To sum up, the system and method for monitoring sport related fitness by estimating muscle power and joint force of limbs has the following advantages:

(1) novelty:

A. it can use an information of two-dimensional (2D) pressuring sensing and displacement detection to estimate the movement of limbs and the changing of body gravity center in three-dimensional space.

B. It can quantify the fitness parameter relating to muscle power and joint force of limbs.

(2) Inventiveness:

A. It is an inventive software technique with fewer sensors required to be worn on a user.

B. By the cooperation of the ergonomic model and the fitness parameter database in the monitoring system of the present disclosure, the muscle power and joint force of limbs can be accurately estimated.

(3) Usability:

A. The monitoring system not only can be applied in the exercise equipment industry for improving fitness or rehabilitation, but also can be applied in medical applications, such as elder care for lower the risk of falling down.

With respect to the above description then, it is to be realized that the optimum dimensional relationships for the parts of the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present disclosure.

What is claimed is:

1. A method for monitoring sport related fitness by estimating muscle power and joint force of limbs, comprising the steps of:
    using a sensing module to obtain sensor values; and
    using a force/track detection module to receive the sensor values from the sensing module to be used as base for estimating feature parameters and classifying a motion series relating to muscle power and joint force of the limbs so as to obtain fitness parameters corresponding to the sensing of the sensor module.

2. The method of claim 1, wherein the limbs include at least one type of limbs selected from the group consisting of: upper limbs and lower limbs.

3. The method of claim 1, wherein the force/track detection module is enabled to tracking an exercise performed by the limbs, including upper limbs and lower limbs, while the detected track is resulting from at least one exercise selecting from the group consisting of: the stretching exercise of the upper limbs and the stretching exercise of the lower limbs.

4. The method of claim 3, wherein the stretching exercise of the upper limbs includes at least one movement selected from the group consisting of: lifting a heavy object, pushing/pulling, punching, racket swinging, and pitching.

5. The method of claim 3, wherein the stretching exercise of the lower limbs includes at least one movement selected from the group consisting of: one foot lifting, one leg squatting, one leg standing, two legs standing.

6. The method of claim 1, wherein the sensing module uses at least one device selected from the group consisting of: a pressure detecting unit, and a position detecting unit, for detecting the sensor values.

7. The method of claim 6, wherein the pressure detecting unit is a device selected from the group consisting of: a pressure mat, a foot pad, and a force plate.

8. The method of claim 6, wherein the position detecting unit includes at least one device selected from the group consisting of: accelerometers and gyroscopes.

9. The method of claim 8, wherein each device included in the position detecting unit is adapted to be arranged at a position selected from the group consisting of: an arm, an elbow, waist, and a knee of a user.

10. The method of claim 6, wherein the sensing module further comprises:
a processing unit, for fetching and synchronizing the sensor values.

11. The method of claim 1, wherein the force/track detection module further comprises:
a parameter calculation module, for fetching the sensor values from the sensing module to be used in a calculation for obtaining a signal capable of defining the tracking of the motion series in the space, as well as in an estimation for obtaining feature parameters relating to muscle power and joint force of the limbs; and
a motion identification module, for performing a matching calculation upon the feature parameter resulting from the estimation of the parameter calculation module and at least one motion track model so as to perform a classification basing on the comparison and thus obtain the motion series to be used for estimating the fitness parameters.

12. The method of claim 11, wherein the parameter calculation module further comprises:
a feature capturing unit, for fetching the sensor values from the sensing module to be used in an estimation for obtaining the feature parameters relating to muscle power and joint force of the limbs.

13. The method of claim 11, wherein the parameter calculation module further comprises:
an ergonomic model database, for storing data relating to ergonomic models to be used as basis for estimating the feature parameters.

14. The method of claim 11, wherein the motion identification module further comprises:
a motion model database, having the at least one motion track model stored therein.

15. The method of claim 14, wherein each motion track model is at least one model selected from the group consisting of: a motion track template, a motion track statistic model, a motion track probabilistic model.

16. The method of claim 11, wherein the motion identification module further comprises:
a match unit, for performing the matching calculation upon the feature parameters resulting from the estimation of the parameter calculation module and the at least one motion track model so as to obtain an optimal motion track corresponding to the feature parameters to be classified into the motion series that is used for estimating the fitness parameters.

17. The method of claim 11, wherein the matching calculation performed by the motion identification module is at least one calculation selected from the group consisting of: a distance calculation and a similarity calculation.

18. The method of claim 11, wherein the motion identification module further comprises:
a fitness parameter database, for storing skill-related fitness parameters while providing the stored skill-related fitness parameters to be compared with the fitness parameters obtained from the estimation of the motion identification module.

19. The method of claim 18, wherein the motion identification module further comprises:
a comparison unit, for comparing the fitness parameters obtained from the estimation of the motion identification module with the skill-related fitness parameters stored in the fitness parameter database so as to output a comparison result accordingly.

20. The method of claim 19, wherein the motion identification module further comprises:
a notification unit, electrically connected to the comparison unit to be used for displaying the comparison result.

21. The method of claim 20, wherein the notification unit is a device selected from the group consisting of: cellular phones, personal digital assistants (PDAs), computers, speakers, alarms, indication lamps, and other audio/video devices.

22. The method of claim 20, wherein the notification unit is connected to the comparison unit through a network system.

23. The method of claim 1, wherein each feature parameter is related to at least one value selected from the group consisting of: gravity center of human body, biped center of mass, displacement of the center of gravity, direction, speed, distance traveled, relative position, coefficient of rigidity, joint angle, variation of joint angle, muscle power.

24. The method of claim 1, wherein the fitness parameter is related to at least one value selected from the group consisting of: muscular strength, muscular endurance, agility, flexibility, muscle power, speed, and balance.

* * * * *